(12) United States Patent
Asprey

(10) Patent No.: US 9,080,982 B1
(45) Date of Patent: Jul. 14, 2015

(54) SPECTROGRAPHIC APPLICATIONS OF TRICHEL PULSES

(76) Inventor: William J. Asprey, Lake Stevens, WA (US)

( * ) Notice: Subject to any disclaimer, the term of this patent is extended or adjusted under 35 U.S.C. 154(b) by 312 days.

(21) Appl. No.: 13/448,331

(22) Filed: Apr. 16, 2012

Related U.S. Application Data

(60) Provisional application No. 61/517,197, filed on Apr. 14, 2011.

(51) Int. Cl.
*G01J 3/30* (2006.01)
*G01N 21/68* (2006.01)
*G01J 3/443* (2006.01)

(52) U.S. Cl.
CPC ............... *G01N 21/68* (2013.01); *G01J 3/443* (2013.01)

(58) Field of Classification Search
CPC ................................. G01N 21/68; G01J 3/443
USPC ......................................................... 356/316
See application file for complete search history.

(56) References Cited

U.S. PATENT DOCUMENTS

| | | | | |
|---|---|---|---|---|
| 3,470,741 A * | 10/1969 | Durbin | ........................ | 73/861.09 |
| 3,559,049 A * | 1/1971 | Liebermann et al. | ......... | 324/464 |
| 4,293,220 A * | 10/1981 | Denton et al. | ................ | 356/316 |
| 5,483,337 A * | 1/1996 | Barnard et al. | ................ | 356/316 |
| 5,565,114 A * | 10/1996 | Saito et al. | ........................ | 216/60 |
| 6,207,008 B1 * | 3/2001 | Kijima | ...................... | 156/345.13 |
| 6,677,604 B2 * | 1/2004 | Mitrovic | ......................... | 250/573 |
| 7,042,159 B2 * | 5/2006 | Tanaka et al. | ............. | 315/111.21 |
| 7,123,361 B1 * | 10/2006 | Doughty | ........................ | 356/316 |
| 7,274,015 B2 * | 9/2007 | Miller et al. | .................. | 250/288 |
| 7,361,514 B2 * | 4/2008 | McLaughlin et al. | ......... | 436/164 |
| 7,397,560 B2 * | 7/2008 | Seaward et al. | ................ | 356/316 |
| 7,763,820 B1 * | 7/2010 | Sommer et al. | ................ | 209/576 |

OTHER PUBLICATIONS

Gravendeel et al. "Fast photon counting in negative corona discharges in the Trichel regime", J. Phys. D: Appl. Phys. 21, 1988, pp. 744-755.*

* cited by examiner

*Primary Examiner* — Michael A Lyons
*Assistant Examiner* — Shawn Decenzo
(74) *Attorney, Agent, or Firm* — Mark Clodfelter

(57) ABSTRACT

A method and apparatus for analysis of an analyte is disclosed. An energy gradient, which may be Trichel pulses, is established in the presence of the analyte so that atoms and molecules of the analyte are excited or otherwise stimulated to emit photonic radiation. The photonic radiation is received, and analyzed to obtain qualitative and quantitative information about the analyte.

13 Claims, 10 Drawing Sheets

SPECTROGRAPHIC APPLICATIONS OF TRICHEL PULSES

CROSS-REFERENCE TO RELATED APPLICATIONS

This application claims the benefit of Applicant's provisional patent application No. 61/517,197, filed Apr. 14, 2011, and which is incorporated herein by reference in its entirety.

FIELD OF THE INVENTION

This invention relates to chemical analysis systems and glow instigation, and particularly to imparting electron or ion energy to induce photon emissions and attendant photonic, electronic, and kinetic energy analysis.

BACKGROUND OF THE INVENTION

The need to identify quantitatively as well as qualitatively different materials on surfaces, in solutions, or in gas mixtures is widely recognized. Identification of molecules, molecular fragments, atomic species, plasma swept or occupied environmental conditions such as temperature (thermal and quantum), ionizing radiative flux, pressure, flow, optical properties, as well as density gradients at a large range of concentrations is of particular interest.

The earliest historical chemical identifications were done with simple dye indicators that provided a color change to indicate a property, such as Ph. Other physical property observations such as color, melting point, miscibility, density, or the appearance of combustion, i.e. visible emissions of fire, provided indications of presence of certain substances or elements. However, these methods are very imprecise and provide minimal information about the actual concentrations of the target species, although fire did provide among the first known controlled light sources; which also indicated the presence of liquid water by extinguishment of the fire light observed with the eye.

Flame colors were later recognized to be an effective indicator of multiple atomic species and even later became relatively quantitative in flame spectroscopy. These flame colors have been applied for entertainment in fireworks for a long time. Relatively large quantities of target species are required for reliable detection due to the very low and dispersed energies of the emitting light and the limited time window for emissions.

Many attempts have been made by inventors to improve detection and emission efficiency, throughput, costs, and lifetime of flame ionization detector designs. Basic problems with current designs using generalized thermal ionization is a lack of directionality of emissions coupled with the inconsistent rates and amounts of completely ionized sample material. Edge effects of reaction chambers, as well as hot and cold spots in combustion processes, contribute to incomplete ionization, distributed emissions, and distributions of effective thermodynamic temperatures within the reaction chamber.

Another form of ionization based detection is Fluorescence spectroscopy, also known as fluorometry or spectrofluorometry. In this technique, light photons are used to instigate boosting of molecular electrons into higher energy levels, as in pumped molecular lasers. These electrons then drop back into lower energy levels while releasing omnidirectional photons of light. These photons are then analyzed for energy corresponding to the energy level change in the molecule. This energy can then be related to the originating molecule type, emission structure, or species.

A major aspect of fluorometry is that there are many vibrational energy levels of target molecules and/or atoms, causing energy of emitted photons therefrom to take corresponding energy values depending on the quantum vibration energy states of the various target species. This variation in the emitted photon energies can be used to elucidate the vibrational, rotational, and vibronic coupling energy separations when there are numerous photons to analyze at all energy levels, with the analysis used for identifying particular molecules, molecular structure, or shape.

Lasers or spectrum sampled broad band light sources, with variable bandwidths of photons, can excite specific and predictable molecular transitions. The advantage to the dispersion or filter separated broadband sources is that they are easily scanned over known wavelengths to create various stimulation profiled emissions. Lasers are typically very narrow energy band photon emitters, although some lasers, such as dye lasers, are tunable to produce photons of a desired wavelength, and thus a desired energy level. However, in any of these methods, difficulties are encountered in tuning or scanning the input stimulation photons to a sample across a waveband and then cross scanning an output emission spectrum analysis from the sample for each input wavelength. Not only do such methods lead to very large, noisy integrated data sets, long periods of time are required to complete an analysis, particularly with a very dilute analyte. Further, the analyte itself may be undesirably modified by the stimulating radiation.

A recognition of these limitations and the requirements of large scale industry has led to several notable improvements, such as multiple band illumination contemporary with multiple excitation regions, multiple detectors, and/or multiple dispersion elements. While these improvements speed up the analysis, they still generate large data sets required to be processed and also require large integration times for dilute analyte analysis.

Lasers, photodiodes, and lamps, particularly xenon arcs and mercury-vapor lamps, are among photonic light sources typically used for sample stimulation. Each of these sources present difficulties such as limited lifetimes, a continuously degrading operational output, high operational temperatures, wide emission bands and other factors that present complexities in industrial practice. Lasers and photodiodes have a very narrow bandwidth output, which may be advantageous in some instances and a disadvantage in other instances. Further, while lasers and photodiodes may be tunable to some extent, lasers and photodiodes capable of relatively large excursions of wavelength are not available. In addition, relatively inexpensive sources of ultraviolet A to vacuum ultraviolet photonic radiation, which would be useful in some embodiments of the instant invention used in a vacuum, are also not available.

These aforementioned methods all use inefficient electrical energy conversion into photonic energy for stimulating molecular emissions, with various schemes for analyzing the resulting emissions. The disadvantages of driving the entire process with photonic energy are that:

(a) The inherent losses due to entropy make these approaches inherently inefficient uses of power. The fact that most of the stimulating energy is lost to heating the sample, heating the chamber, or leaving the environment cause these methods to be systematically inefficient. This waste of energy is particularly unfortunate where portable applications are needed, or low analyte concentrations are available, which may require long integration times.

(b) The material and financial costs of these approaches are very high due to esoteric material requirements for light sources, complex fabrication requirements, short lifetime of stimulating elements, hazardous and esoteric material use, and other manufacturing and material limitations.

(c) The reaction chambers must be made of wide band transparent materials, which typically are expensive consumables.

(d) The photonic nature of the sample stimulation also suffers from Rayleigh and Raman scattering. Like the signal emissions, this undesirable scattering of the stimulation and generally longer Raman wavelengths is omnidirectional. This causes excess photon counts and mistaken counts due to Raman shifted wavelengths overlapping true electronic transition emissions on the detectors.

(e) The ideal energy efficiency for light emission is decremented by both the emission process itself as well as inefficiencies of the production of the stimulating radiation. This makes the overall system efficiencies very poor for photon stimulated photon emission use as a sensible light source.

Electron impact ionization is a technique in which high kinetic energy electrons pass near or into target analyte molecules, with the electrons inducing ionization, excitation, and/or some or complete molecular fragmentation, depending on intensity and energy levels of the electron flux. Near molecular collisions by highly energetic electrons causes large fluctuations in the electric and relative magnetic field around the neutral molecules and induces ionization and fragmentation. This process is used to prepare samples for induction into mass spectrometry analysis. As is currently practiced, electron ionization is not viable for inducing characteristic photonic emission from affected analyte molecules and atoms.

Laser induced breakdown spectroscopy (LIBS) is a method in which short, narrow band intense laser light irradiance of a sample surface ablates a small amount of sample material to a thermal plasma. This plasma then emits relaxation spectra that is analyzed for atomic emission content with or without crossed secondary lasers. This technique depends on complete molecular disintegration and generalized atomic ionization so that only atomic emissions are utilized. Reproducibility of the results is sometimes limited due to variation in the laser coupling and resultant plasma. Coupling LIBS capabilities with free high energy ion or electron impact plasma maintenance or subsequent plasma process is envisioned as an analyte induction or preparation method to interface with this electric discharge invention.

SUMMARY OF THE INVENTION

This method establishes a train of energy gradients in the presence of an analyte to induce spectral emission of atoms and molecules in the analyte. The emitted spectral lines are obtained, and analyzed to obtain information related to at least one component of the analyte.

DETAILED DESCRIPTION OF THE DRAWINGS

Figure 1:
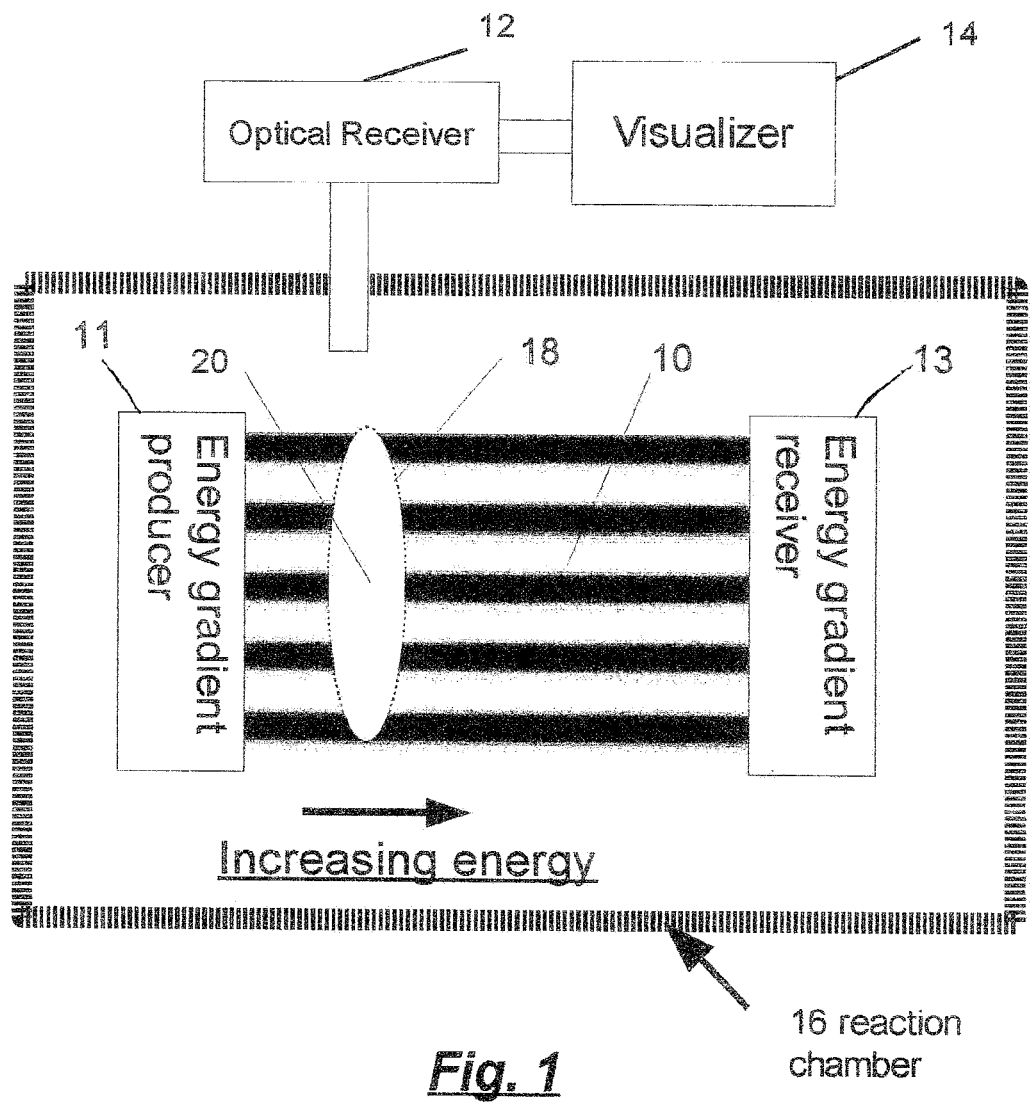
FIG. 1 is a diagrammatic view illustrative of the instant invention.

Referring initially to FIG. 1, the disclosed invention is an apparatus 16 and method for using time and space varying energy gradients 10, produced by energy gradient producers 11 and 13, and which may produce unevenly accelerated electrons or ions or pulsed spectral sweeps, inducing stimulated and ionic plasmas 20 from which spectrographic analysis of spectral lines may be obtained. In other words, and by way of example, a plasma field 20 is established, and may have a lowest energy level on one side, such as a left side thereof, and a higher or highest energy level on the other side, such as a right side thereof, establishing an emission energy gradient in the plasma field. A sample to be analyzed is in the energy gradient of the plasma field, and which is exposed to respective energy levels from lowest to a highest. An optical receiver 12 receives spectral emissions from the plasma field, and a visualizer 14 analyzes and displays, or otherwise is used to infer molecular and atomic constituents of the sample, herein also designated as an "analyte". Methods of producing time and space varying energy gradients that produce analyzable emissions are an electrical field, interactions of gas volumes with pulsed ion or neutral atomic or molecular beams, ion or electron accelerator pulses, distributed chemical reactions, and ablation ion release from laser pulses on surfaces.

Figure 2:
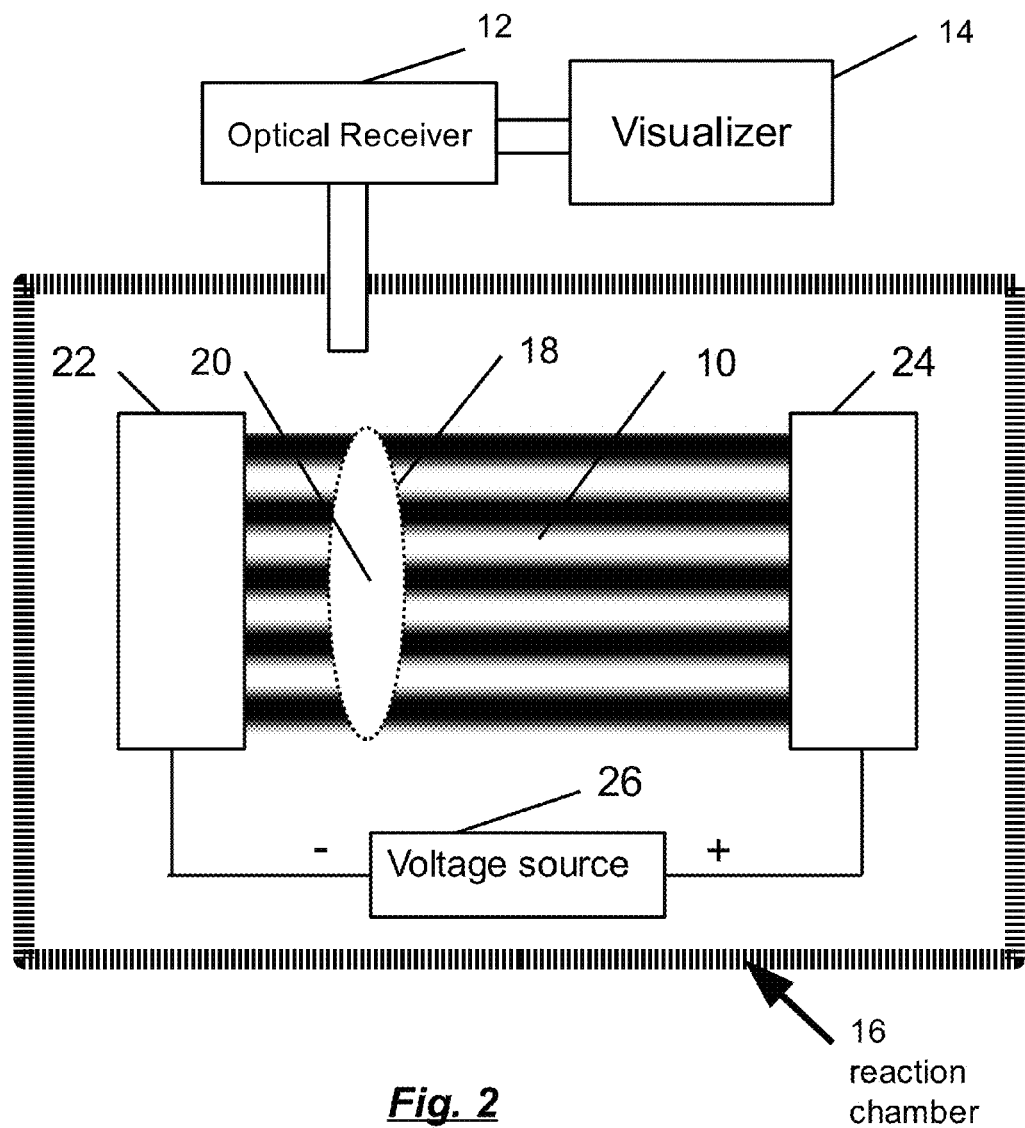
FIG. 2 is a diagrammatic view more specifically denoting the components of FIG. 1

Plasma pulses of the instant invention may be very low energy phenomena on the order of nanojoules input per pulse. A large number of similar or the same sequentially occurring energy gradients need to be established and integrally observed to establish sufficient signal at each spectral line for successful chemical analysis. Trichel pulse emissions 20, as shown in FIG. 2, produce such repeating similar time and space varying energy gradients and result in plasmas 20 which are easily induced when a voltage difference of sufficiently high voltage potential is applied by voltage source 26 between at least two electrodes 22, 24 so as to cause a glow, or corona, indicated by dashed lines 18, between the two electrodes or around one end of one of the electrodes. The gap between the electrodes is referred to herein simply as a "gap". The Trichel pulse plasma glow was first observed by Michael Faraday in January of 1838, and was assumed to be a continuous glow. However, studies performed by G. W. Trichel in 1938 showed that rather than a continuous glow, the corona glow was actually a series of fast, regularly occurring electrical discharges, typically occurring in the low or sub-megahertz range pulse rate. Duration of the pulses may be from a few to several dozen nanoseconds depending on a number of parameters, such as properties of the matter in the gap, electrode geometry and spacing, and potentials applied between the electrodes. Pulsed plasma generation by other particles with time and space varying energy gradients 10 can be driven at any pulse rate, allowing the distributed particles with time varying energy gradients 10 to instigate stimulated photon release in time and space within a repeatable plasma emission envelope 18. The required energy gradients, which may be less than 1 electron volt to hundreds of electron volts will stimulate a broad range of emissions from the materials suspended in the plasma region. Trichel pulses are known to occur only for moderate pressures from less than 1/10th atmosphere to several atmospheres, while other energy gradients can repeat even faster.

The frequency of Trichel pulses appears to be mediated by development of distributed space charges from electron and induced ion distributions with velocities that correlate with external electrical field strength gradient exposures and magnetic interactions. The reaction products, as excited, fragmented, and ionized molecules or atoms, and electrons in the plasma that detectably respond to the electron flow are then removed or swept from the gap by drift and diffusion, allowing electrical field strengths to again increase for another pulse within a microsecond or so. In other words, the reaction products caused by plasma formation effectively increases electrical resistance in the gap, which reduces electron flow and quenches the plasma. As the reaction products clear from the gap, electrical resistance lowers and another Trichel pulse occurs with the electron swarm again obtaining time and space varying energy gradients 10 which interact in the plasma fields to produce time and space varying energy gradients 10 in all ions in the gap as time continues within each pulse. During the intervals between Trichel pulses, the sample gas flows back into the gap, automatically charging the gap with the sample gas. As such, the same spectra indicative of the sample occurs with each Trichel pulse.

FIG. 1 also instructs the application of an optical receiver 12, which can be implemented by induction optics trained at a location within the pulse emission 20 and feeding a spectral disperser in the form of filters or dispersion gratings or prisms. The output from this receiver 12 is passed to visualizer 14, which converts the spectral energy into human or machine readable visual or electronic output form, and which is indicative of the chemical species present in the plasma field.

The functions of the receiver 12 and the visualizer 14 could also be implemented with spectra-sensitive solid state devices or chemically responsive films that provide a visual or electronic signature of unknown analyte for identification. In one embodiment, component volumes, sizes, and weights are minimized, providing a small, easily portable plasma spectrographic visualizer as in FIG. 2, coupled optically with a spectral disperser and a small, very low power Trichel pulse plasma generator. This instrument carries a small high voltage power supply 26 that energizes electrodes 22 and 24, resulting in a discharge plasma volume 20, and optical receiver 12 coupled to an intensifier visualization device 14. This combination of components can be manufactured to weigh less than 10 pounds and be less than 20 cubic inches in volume to allow easy portability for chemical detection. As noted, electrons flowing through the plasma field or envelope 18 are initially moving relatively slowly, and have less energy, just after they leave electrode 22, and are accelerated toward electrode 24 through plasma field 20, thus acquiring additional energy and providing stimulation energy as they move across plasma field 20.

Figure 3:
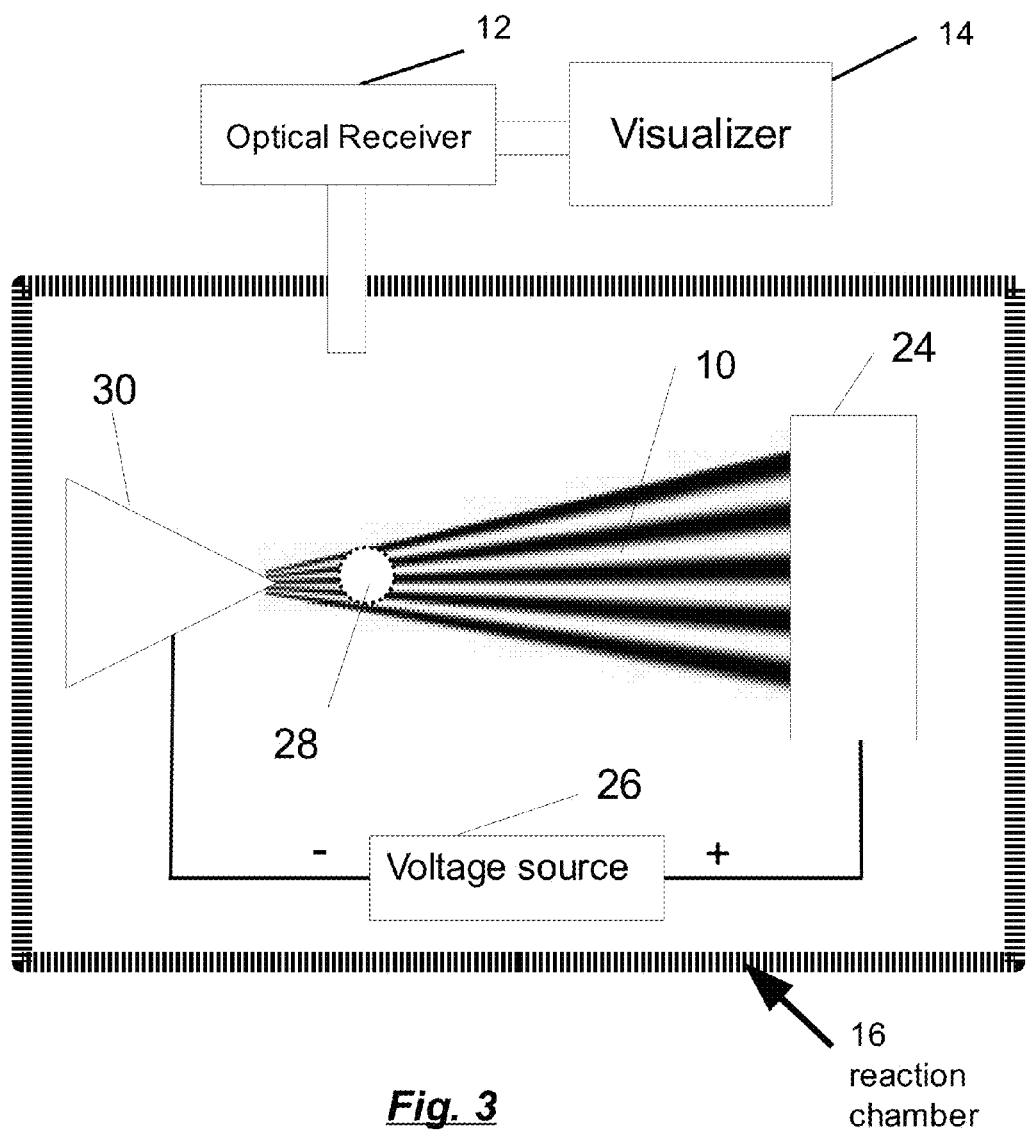
FIG. 3 is a diagrammatic view of another embodiment of the instant invention.
Figure 7:
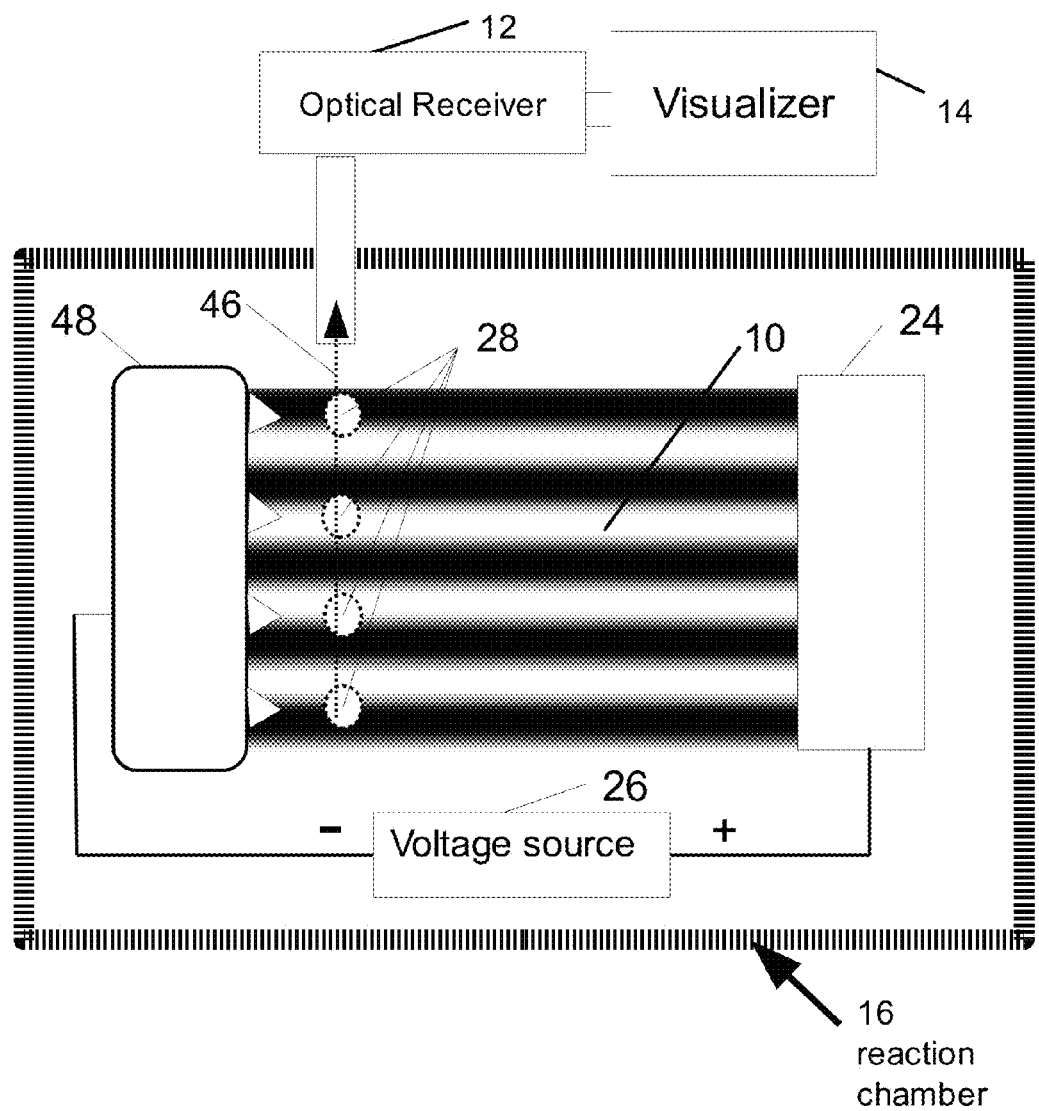
FIG. 7 is a diagrammatic view of another embodiment of the instant invention.
Figure 8:
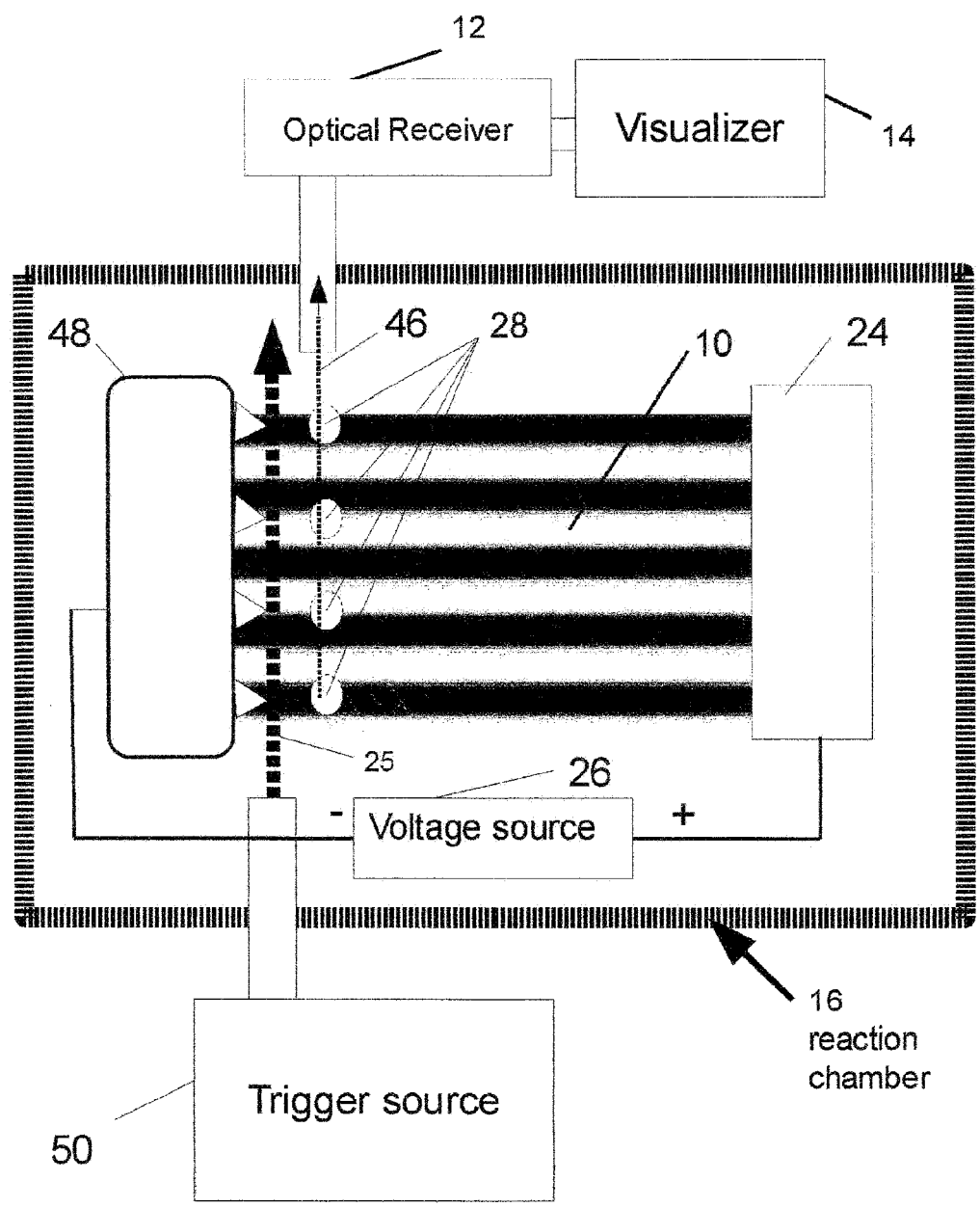
FIG. 8 is a diagrammatic view of a triggered embodiment of the instant invention.
Figure 9:
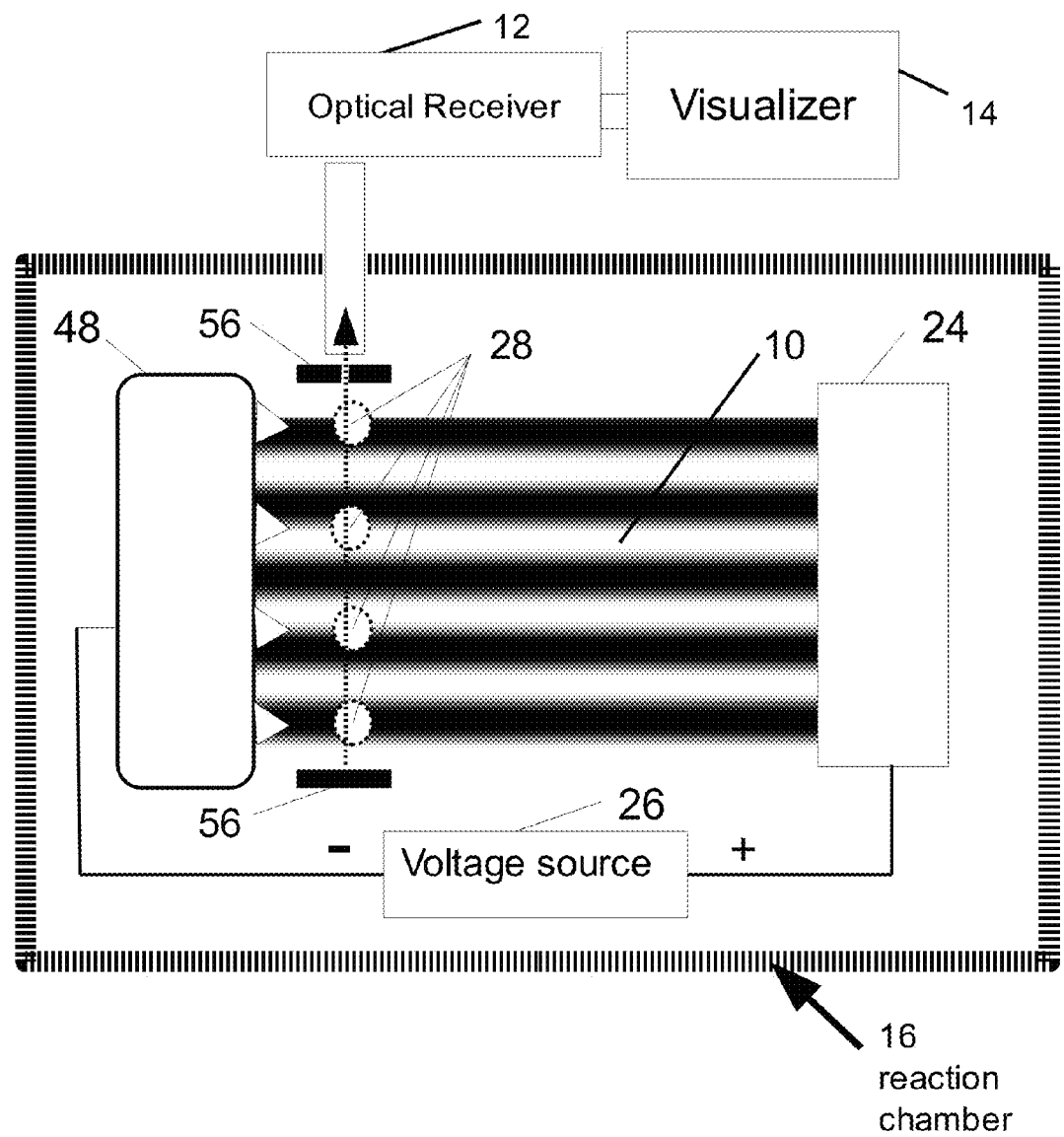
FIG. 9 is a diagrammatic view of a laser pumping embodiment of the instant invention.

In FIG. 2, current flow between electrodes 22, 24 resulting from naturally occurring discharges (Trichel pulses) is typically seen to be an irregular sawtooth pulse pattern, with peaks thereof representative of periods of highest electron flow between the electrodes. As such, from initiation of a Trichel pulse, electron density in the plasma increases to a peak, at which point electron energy gradients reverse and electron flow terminates. For purposes of this invention, and by way of example only, one of the electrodes 24 may be configured as a plane, and the other negative electrode 26 having a smaller prominence, such as the end of a point as shown in FIG. 3 with concentrating electric field lines giving rise to very high time and space varying energy gradients for electrons sourced in the Trichel pulse by the negative electrode. Other electrode configurations may be used, including arrays of multiple points on a more negative electrode 48 as illustrated in FIGS. 7, 8, and 9.

Rounded points and shaped counter electrodes can be applied to produce differently shaped plasma envelopes as illustrated by the difference in appearance of the plasma region 20 in FIG. 2 and the plasma region 28 in FIG. 3. The planar electrode 24 and more pointed electrode 30 are spaced apart, with a gap space therebetween on the order of hundreds of small point 30 diameters wide or less, and which may be on the order of less than a centimeter to more than 10 cm with sufficiently large applied voltage differences resulting in sufficient electric field gradients to produce Trichel pulses. At atmospheric pressure and gaseous environment, Trichel pulses will appear between a couple thousand volts potential difference with small gaps, such as the aforementioned centimeter or so, and will require up to tens of thousands of volts for larger gaps or less pointed more negative impressed voltage electrodes 22.

The negative relative voltage is applied to point electrode 30, and near the point thereof forms a concentrated electrical field with respect to the planar electrode 24, as shown in FIG. 3. In gaseous environments above 1/20th of atmospheric pressure, as this negative potential is increased, a breakdown or cascade threshold is reached at which negatively charged electrons are forced from point electrode 30 toward the positively charged planar electrode 24. These electrons experience very rapid, changing acceleration, and thus an increasing energy level, as they move through the rapidly diverging electric field. The electron flow from point electrode 30 is energized to an extent that the electrons of the electron flow collide with atoms and molecules of air and analyte in the gap to create a discharge glow region 28. The plasma field is a highly chaotic state of matter in the glow regions 28 in which some of the atoms and molecules in the gap are fragmented and the various molecular species stimulated or ionized to have lost or gained one or more electrons due to collisions producing time and space varying energy gradient particles flowing across plasma volume 28, and are thus charged positively, negatively or obtain no net charge.

Figure 10:
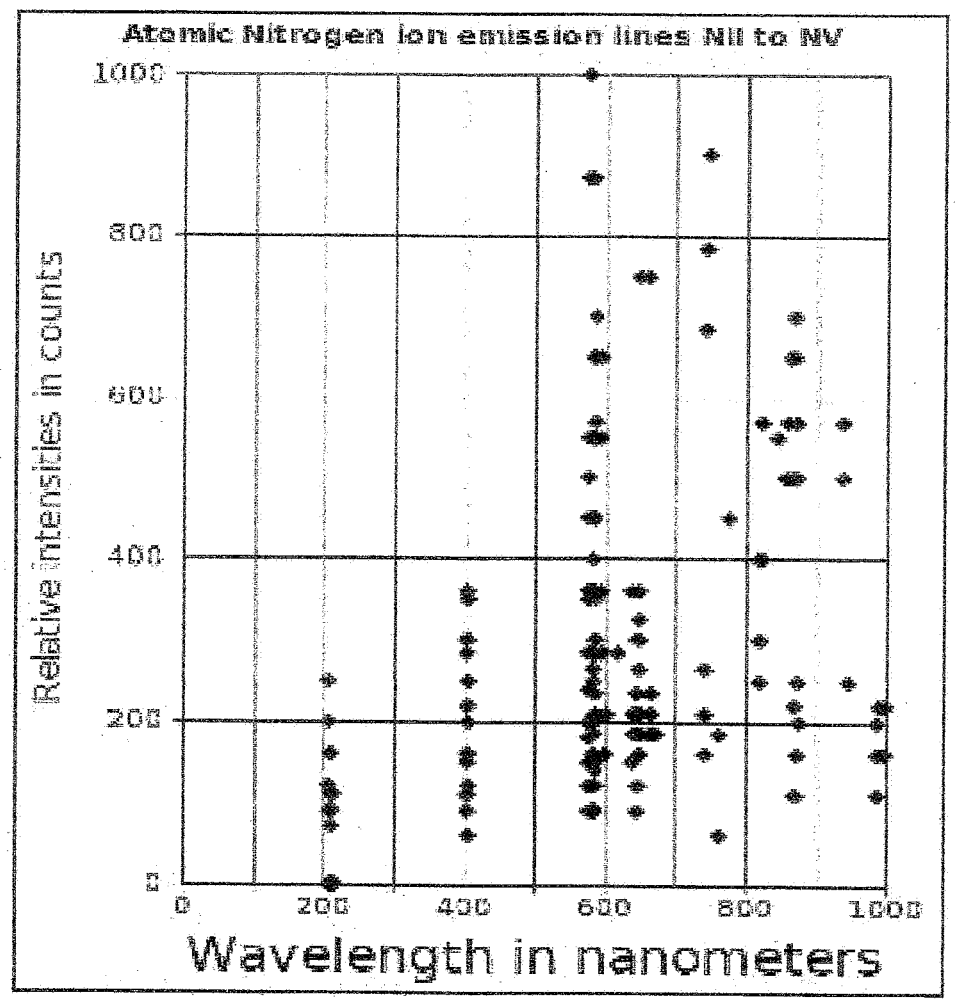
FIG. 10 is a graph illustrating emission lines of atomic nitrogen as may be obtainable from the instant invention.

While in the plasma state, some of the atoms, molecules and molecular fragments in the plasma volume 28 have bound electrons that, when struck by an electron or other particle of a specific energy level, i.e. a "quantum" of energy, absorb the quantum of energy, as illustrated in FIG. 10 for atomic nitrogen. The ions of nitrogen have many ionization states, resulting in the bound electrons being kicked into a higher energy state, or orbital, from their ground states. When the bound electrons relax, or returns back to their lower energy states, a light photon is released in the discharge glow region 20 emitting the absorbed quantum of energy with recognizable quantum energy changes from rotational, vibrational, and electronic (rovibronic) transitions. These released photons are responsible for the corona glow, and are of various discrete wavelengths, each wavelength correlating with the specific quantum of energy from which the respective photon was created from the stimulated molecule or atom relaxation. As each element and molecular orbitals are associated with specific wavelengths, it has been discovered that, by analyzing the various wavelengths emanating from the plasma generated by Trichel pulses at specific locations and times during a single or repetitive pulses that the various components of an analyte, and respective quantities thereof, may be ascertained by comparison with standards or by prediction from theoretical energy transitions.

Significantly, it has been found that the plasma fields of the instant invention do not glow uniformly throughout their volume. Instead, different regions of the plasma fields glow with different wavelength strengths, these regions being remarkably repeatable from pulse to pulse in the presence of an analyte of interest. The probable reason for this nonuniformity is that the electrons are being constantly accelerated as they move through the gap, and thus have different energy levels at different distances from the electrode producing the plasma field. As such, at a distance from the electrode corresponding to a quantum level of energy (from the electron flow) absorbable by a target atom or molecule of the analyte, the target atom or molecule will absorb a time and space varying energy electron and emit one or more spectral lines indicative of that particular atomic or molecular species. Similarly, molecular fragments and ions in the plasma field likewise respond to the time and varying energy of the electron flow at discrete locations in the plasma field, and may glow or fluoresce at their own respective wavelengths, or vibrate, rotate or provide other detectable indications of their presence. Here, vibrations and rotations of molecular ionic species and fragments in the plasma field typically emit radio frequencies that may be detected and analyzed. In this case, receiver 12 would be a radio receiver equipped with an antenna instead of an optical receiver.

In one embodiment, and where photons are being analyzed, a spectrometer, such as an Echelle spectrometer, is applied as the optical receiver 12 and is mounted to receive and analyze light from the plasma generated by Trichel pulses. An Echelle spectrometer allows imaging of very wide band spectra on single 2D detector areas for compact and efficient analysis. In other embodiments, a spectrometer using simple single order dispersion is also workable. The entrance slit of sampling optics of the spectrometer optical receiver 12 are configured to focus on a very thin sampling width, such as about a micron or so, and may be initially aligned toward the plasma region closest to the electrode. The closest region for sampling of the plasma field may be as close as about 10 microns from the electrode. At this sampling region, and as noted, electrons have just left the negative electrode, and are at their lowest energy levels. From that point, also as noted, the electrons are being constantly and rapidly accelerated through the gap under the electrical influence of the opposite positive electrode. The spectral signatures for emissions at this closest region are recorded over the course of many pulses, and the slit aperture is moved to focus on the next region, which may be 20 microns from the negative electrode. As noted, the spectral signatures change over the time course of each pulse at each selected location in the plasma field, and are remarkably constant and repeatable between discrete pulses. As such, the emissions may be recorded as spectral line signatures developed over the duration of a plurality of many pulses at each selected location. This provides average time evolution data for every wavelength at each selected location monitored by the spectrometer, some of which wavelengths variability will determine chemical identities and quantities, along with information characteristic of pressure, temperature, and dynamic states of materials in the gap, such as Doppler broadening and vibrational quenching effects. In other embodiments, a single location may be sampled only once or a few times, for instance less than 10, before the next selected location is sampled. These embodiments may be useful when specific elements or compounds are being scanned for, such as elements or compounds found in explosives, such as nitroglycerine or the like, or poisons, such as organophosphates or other toxic compounds. In addition, where there are specific locations in the plasma field where it is known a priori that certain elements or compounds of a desired analyte to be found will emit photons, then only those selected locations may be sampled in order to more rapidly scan for the desired analyte.

Figure 4:
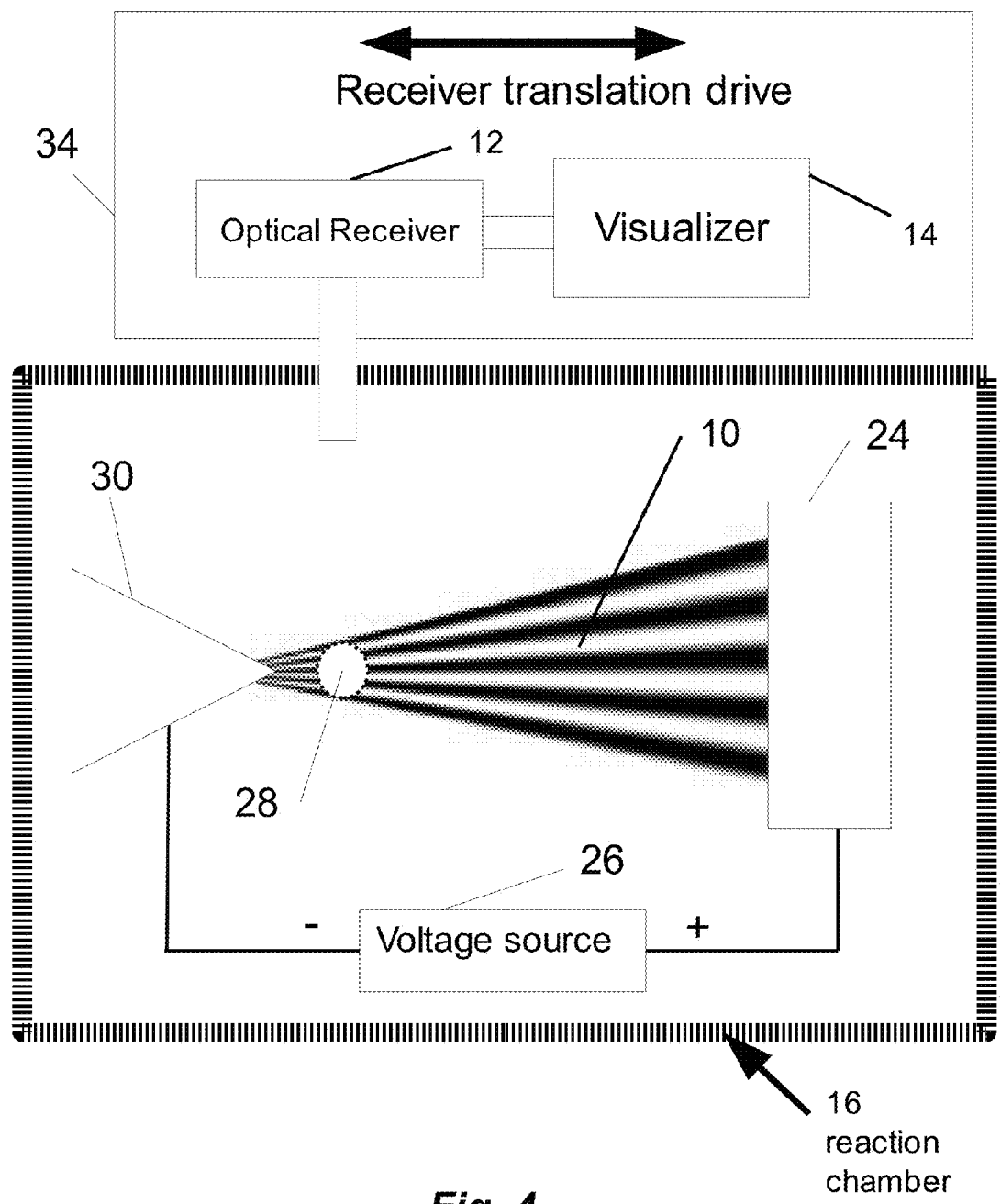
FIG. 4 is a diagrammatic view of additional features of the embodiment of FIG. 3.
Figure 5:
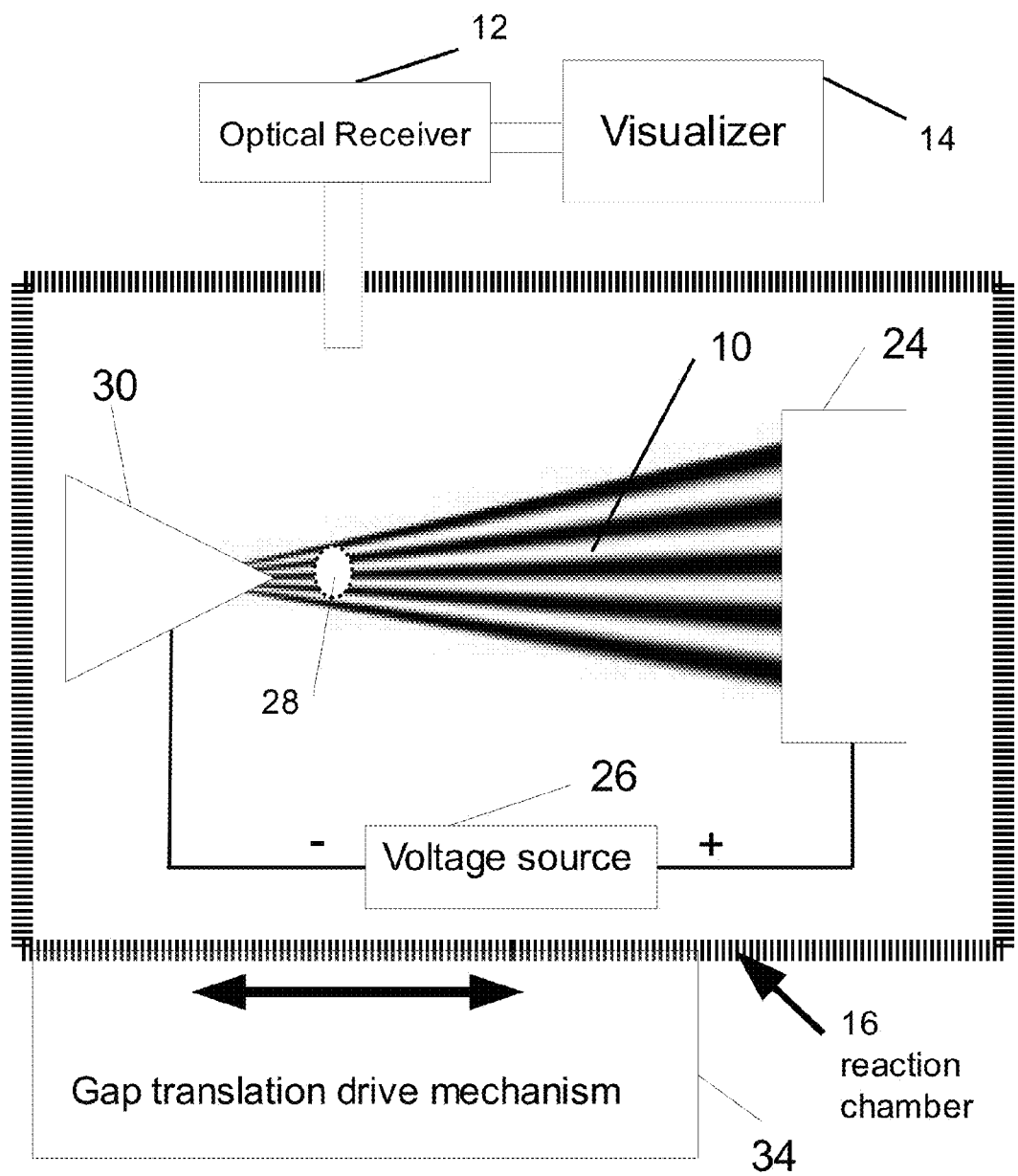
FIG. 5 is a diagrammatic view of additional features added to the embodiment of FIG. 3.

For moving the optics of a spectrometer as optical receiver 12, a receiver translation drive mechanism 34 alters, in some embodiments, the location of the photon sampling optics to focus on the next selected location within the discharge emission 28, as shown in FIG. 4. In other embodiments, the spectrometer optics may be stationary, and the electrodes may be moved relative to reaction chamber 16 by operating a gap translation drive mechanism 36 relative to the optical receiver entrance optics, thus moving the plasma field to sample different selected locations along the plasma emission envelope (FIG. 5).

Figure 6:
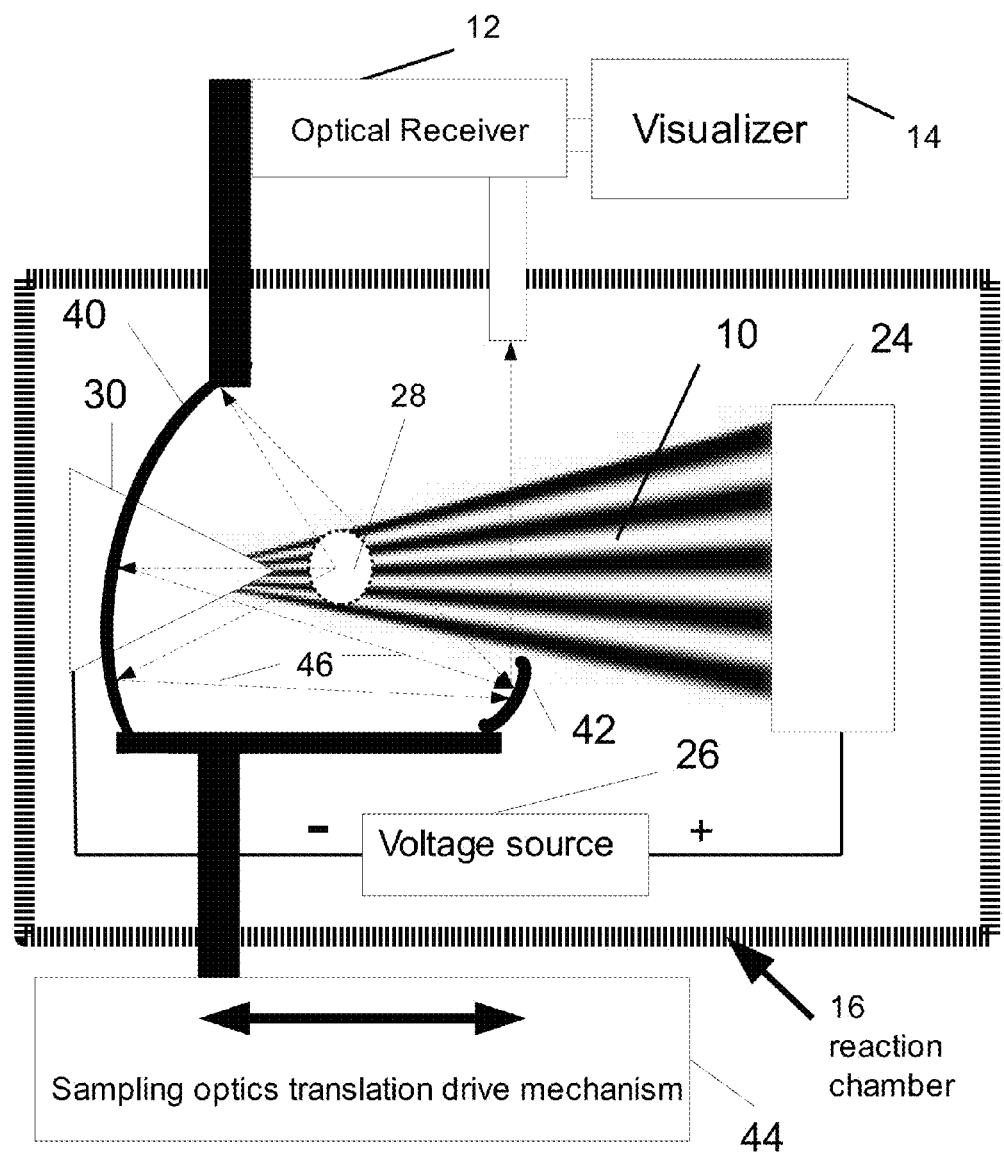
FIG. 6 is a diagrammatic view of yet another embodiment of the instant invention.

Additional methods of sampling the discharge emissions include the use of gathering optics, such as a parabolic reflector 40 or convex transmission optics, which provide collimation of the light from very small regions of omnidirectional emissions near the focal point within the stimulated region, as is practiced in confocal microscopy. The sampling optics translation drive mechanism 44 can be operated to scan selected discrete locations within the glow region 28 by moving the gathering optics 40 and 42, optical receiver 12, and visualizer 14 as a unitized group described with structural units in FIG. 6.

Mechanisms 34, 36, or 44 may be configured to provide a stepped translation yielding spectra at each selected location as the mechanism steps one or more micron at a time along the discharge envelope, or may be configured to provide a dynamic sinusoidal reciprocating motion or directional sweep for scanning the discharge envelope to convolve with acquired spectral signatures. As noted, and in some instances, mechanisms 34, 36, or 44 may be used in conjunction with a computerized library of spectra, which is obtained empirically, to automatically cause mechanism 34, 36, or 44 to step to predetermined selected locations in the plasma field or envelope. In other instances, mechanisms 34, 36 or 44 may be used to sequentially step through each location in the plasma field. This embodiment would be useful in research, or in acquiring spectra from known samples in order to build a library of spectra indicative of compounds and elements of interest.

In some embodiments, Trichel pulses may be triggered, as by directing very short subnanosecond laser or other beam pulses on the negative electrode 22, 30, or 48 to create free electrons that initiate a cascade of electron flow and subsequent Trichel pulses 28 at rates above 10 MHz or less as in FIG. 8 with a multi-point electrode 48. In this instance, the voltage potential applied by voltage source 26 between the negative electrode 22, 30, or 48 and positive electrode 24 may be controlled to rise to just below a breakdown potential prior to triggering the pulse. The beam trigger pulse 25 from trigger source 50 is then directed at the negative electrode just before a Trichel pulse would otherwise occur, causing the next Trichel pulse to begin due to the trigger pulse 24.

Among the advantages of using triggered Trichel pulses are that since timing of the pulses is precisely controlled, an observation window for a spectrometer can be opened so that the detector only detects light produced by the Trichel pulse or only part of each pulse. This greatly increases signal-to-noise ratios by eliminating all but a small portion of continuous background light. In addition, triggering allows known Trichel pulse formation under normal conditions which is altered by radioactive ionizing radiation in predictable and analytical ways such as extra or unexpected triggering which can be related to specific ionizing radiation fluxes. As such, the apparatus can be used as a radiation monitor selectably sensitive to different types and intensities of radiation. Here, the negative electrode may be constructed of or include a material sensitive to a particular type of radiation, and which would prematurely induce a cascade of electrons when in the presence of a specific type or quantity of radiation; the more premature the pulse the greater the radiation flux. Sensitivity may be varied by varying gap characteristics, such as distance between the electrodes. Also, predictable triggering allows timing controls of the acquisition system window to exclude the trigger emissions while including all the emitted light from the subsequent pulse as it develops over time. It also allows faster pulse frequencies than natural event triggering entails. In addition, such triggering allows precise timing to capture any "afterglow" fluorescence that may occur after termination of a Trichel pulse as excited electrons fall back to their ground state.

A light source used to generate a trigger pulse may be a shuttered continuous wave laser, a short pulsed laser, or continuous illumination of the electrode with sufficiently energetic coherent or incoherent light to provide pulse-initiating photo-electrons when the gap clearance allows for another Trichel pulse to form without broad band obscuration of the light emission from the pulse. The light from another Trichel pulse or the delayed emission from the previous pulse can be used to stimulate further pulses as well as stimulation of specific energy levels for laser pump action.

Other mechanisms to accurately trigger a Trichel pulse that may be used in the instant invention are radioactivity, thermal emission, sonic shock waves in the electrode or gap, ballistic or driven projectiles, transient applied fields, electrode geometry changes, and impinging ion or electron beams.

From the trigger of the pulse, the electrons spread outward with time and space varying energy gradients from the electrode with ever increasing energies driven by the electric fields. Emissions from regions within the discharge plasma envelope move away from the electrode and occur later in time due to differing time and space varying electron energies driving molecular stimulation leading to fluorescence and ionization emissions. Further out from the negative electrode, molecular fragment and reactive intermediate emissions occur, and ultimately at the furthest reach of the plasma envelope, complete molecular dissociation with atomic ion emission occurs as the distance from the electrode increases from a few microns to several hundred microns away from the electrode. Over time, each pulse develops different energy level transitions beginning from low energies of less than one eV to relatively high energies of hundreds of eV and more. As stated, the respective energy levels are specific to each spatial region within each pulse as time progresses due to the interaction of the thermal, stimulated, and driven materials in the plasma region with electrons having time varying energy gradients. These emissions age with the plasma pulse as electron and ion energy levels encounter negative energy gradients with plasma development and the emissions follow chemical specific extinction pathways as the pulse dies off and the gap clears of non-zero net charges.

In other embodiments, triggering may be omitted and the Trichel pulses may be allowed to occur naturally. The pulses could be recorded in visible and non-visible spectra of interest, and analysis performed only on those recorded portions of interest. Of course, where specific elements or compounds of interest are being detected or observed, only those specific wavelengths would need be scanned for.

The current is very low during the time the activated plasma gap charge distributions are shielding the electrode potentials and rises quickly when the gap clears of distributed space charges, allowing occurrence of another Trichel pulse. These Trichel pulses occur every few microseconds naturally and can be triggered artificially more quickly, depending on the time for gap ion clearance as well as the delay for a cascade stimulating event or trigger, and last for a few nanoseconds each. During each pulse, there is detected a highly specific light emission from atomic and molecular fluorescence. This invention is concerned with emission phenomena induced with the electrons, ions, molecules, and possible molecular fragments or sputtered electrode materials produced by time and space energy gradient regime, and especially the wide range of energies the bombarding time and space energy gradient carriers gain and couple during the pulse generation process.

The initial phase or suspension of the target analyte or containment matrix is inconsequential. Vapors can be injected or diffuse into the gap, liquids can be nebulized, sprayed, evaporated, or injected into the discharge chamber, and solids can be evaporated, ground finely and inducted, or heated to produce vapor or plasma for induction into the discharge plasma chamber. Some of all of the materials in the plasma volume will be stimulated or ionized by the plasma pulse resulting in analytical emissions.

As stated, if an exogenous ionizing radiation flux is sufficiently high it will trigger altered timing of the pulses that are diagnostic of the ionizing radiation, as with a geiger counter. The invention will continue to function as a chemical detector until the ionizing radiation levels reach acute toxic levels. Variation in the gap geometries, the electrode geometries, the voltage waveforms applied to the electrodes, the magnetic environment of the plasma, and gap filling sample and resulting plasma qualities all effect the emission patterns and required driving voltages for triggering. These applied voltages can be automatically corrected to provide Trichel pulses by controlling the electrode potentials upward until triggering a stable series of plasma pulses. Magnetic field plasma interactions and pulsing alters the plasma emissions over the time of the pulses as well, yielding evidence of rotational states of compounds in the analyte by long wave radiation analysis, typically in the radio spectrum.

Another embodiment is to move the electrodes 22 or 30 and 24 relative to each other at set potential differences until stable triggering is achieved. The triggering rates may need to vary because different molecular masses of the target analyte may require more or less time to exit the gap, especially those molecules or fragments that are very massive and neutral. Slower or faster triggering is desirable also for delayed fluorescent afterglow emission analysis and for defining data acquisition and amplification windows.

The electrons accelerating into the gap will also produce a magnetic field that will propagate outward at the speed of light, very much faster than the speed at which the electrons travel. Both the magnetic and electric fields, as well as the electron and ion masses, will encounter and effect materials and net applied fields in the gap. They also will impact neutral and ionized materials in the gap, both elastically and inelastically as they exhibit sufficient field strengths and kinetic energies due to time and space energy gradient variations.

The radiative glow used in the instant invention for analytical purposes and lighting is due to kinetic, electric field, and magnetic effects of ions, stimulated materials, and electrons in the gap, which molecules and atoms then emit photons as they relax toward their ground states during a plasma pulse. Each pulse contains around one nanojoule of total input energy which is less energy than what would typically be required to initiate detonation and combustion within explosive and combustible environments.

Charged species interactions with an average molecule or atom positioned within the gap will couple a continuous range of time and space varying excitation interaction energies to the molecule or atom due to the spatial variations possible for the molecular or atomic and exciting electron or ion separations, especially elastic scattering. Volumes in the gap sufficiently equidistant from negative electrodes will contain molecular and atomic species with a wide variety of energies, emitting lower energy photons from lower energy transitions no matter where they exist in the orbital energy structures of different materials. Inner shell orbitals can be ionized, allowing fluorescence to occur from such inner shell electrons falling back to a ground state after being energized by a plasma pulse.

While the electrostatic electric fields of the charges will be constant as they translate the gap, the magnetic fields will increase along with the kinetic energy of the input charges. With the velocity of net electric charges being much less than the speed of light, the electric field and magnetic fields due to charge 'q' predicted by Maxwell's equations can be approximated in text format as:

$$E=(q*r)/(4*3.14159*\text{Epsilon}*|r|^3)$$

$$B=(mu*q*vXr)/(4*3.1415988*\text{Epsilon}*|r|^3)$$

In which E is the predicted vector electric field, B is the predicted vector magnetic field, q=the electric charge, r=vector distance from q, v is the vector charge velocity, epsilon is the permittivity of free space or the gap environment, and mu is the permeability constant within the gap.

A statistical distribution can now be described for electrons moving relatively to distributed target analyte molecules or atoms at varying distances as they translate under the impressed electric field. Since the electric fields due to the electrons are constant and moving with the electrons, and the magnetic fields are increasing with the velocity of the electrons, the interactions of the electrons with the analyte material will be due to a nearly unlimited variety of field strengths and exposure scenarios, leading ultimately to complete dissociation and atomic ionization of the analyte material in the plasma volume. With assumed random analyte distribution this yields non-uniform stimulating electric and magnetic fields for anisotropic electron energy distributions provided by the complex dynamics of the plasma pulses.

So the scenario within the accelerating charge density in the plasma region is that analyte materials are experiencing an increasingly extreme variety of impact, electric, and magnetic stresses. These stresses result in forces on charge distributions within the analyte material with concomitant energy transfer due to the work of the force and charge displacement. The magnitude of these forces depends in large part on the dielectric constant of the material in question. All substances have dielectric constants greater than pure vacuum, which is defined as unity dielectric constant, so all substances will respond to this excitation with unique spectral line patterns. When a train of energy gradients is sufficiently high, or when multiple interactions on single analyte targets sum, then complete ionization of least bound electrons will occur. Additionally, inner or molecular bonding electrons can be harmonically stimulated to ionize completely or change bond character or orbital energy level. Bonds are resonantly broken or stimulated by moving sequentially occurring train of energy gradients field effects resonating with the harmonic of the energy state and providing the necessary quanta of energy from the charge kinetic source. Chemical catalysis is provided by stimulation of intermediate states leading to reactive intermediates, and finally to reaction products.

In the Trichel pulse regime, ionization begins as noted above. Once ionized, the molecules, fragments, or atomic species obtain a stimulated net positive or negative discrete charge, which causes them to accelerate toward a respective electrode depending on total vector plasma fields at the charge, including the electronic current fields, other ion fields, and the variable integrated impressed total vector of electric and magnetic fields. The released electrons from positive ions join the general free electron drift current with lesser kinetic energies along with negative ions with lower acceleration per charge due to greater mass. This adds to the fields of sequentially occurring train of energy gradients stimulating electrons as they continue to be accelerated. The relative mass ratio of the electron to the ion is always very small. This implies that the physical spatial movement of the charged ions will be far less than that of the electrons over time, since the forces on the two will be the same magnitude but in opposite directions for singly positively ionized states. As this process of electron injection and acceleration continues over a few nanoseconds, the amount of ions continues to increase throughout the plasma volume, effectively polarizing the gap volume against the impressed field and driving the electronic and ionic energy gradients to negative. The resulting state of near zero current flow lasts for time intervals on the order of microseconds. However, this effective gap current block is unstable, possibly due to inflow of analyte. The ions and electrons that are still in the gap field will slowly drift toward their respective attractive electrode and mutually interact or drift from the gap. Of course, impressed fields can be varied to accelerate or retard the ion and electron clearance from the plasma gap to repeatedly expose the neutral fluorescing samples or remove formed ionized fragments, molecules, or atoms.

It is believed that the actual timing of the pulse initiations are not just dependent on clearance of the charged species from the gap volume. Due to electronic binding energies in the bulk material of an electrode, there needs to be an energetic trigger or quantum mechanical tunneling effect to allow an electron to escape from the surface of an electrode into the bulk field of the gap volume to initiate another Trichel pulse ionization cascade. It is thought that this can be initiated by stimulation of the surface of an electrode as with a trigger as described, random or analytical ionizing radiation excitation anywhere in the gap, or other energetic stimulation of electrons or ions from the surface of the electrode such as heat, mechanical movement, acoustic stimulation, or pulsed electric or magnetic fields.

Photon emission occurs nearly simultaneously with and during the current pulse leading to longer time delayed fluorescence as well. A fraction of the ions contacting the negative electrode could carry sufficient kinetic energy to predictably trigger the next pulse of electrons. This may be used analytically for ion detections based on time of translation from the plasma volume to the negative electrode, and where desired, may be corrected for by calibrations of the times for arbitrary standard materials and conditions. In any case, the phenomenological characteristics of the Trichel pulse emissions are similar from pulse to pulse and are useful for this analytical method. Spectral analysis of emitted photon energies during a Trichel pulse, and in the presence of an analyte, at varying times and locations in the plasma volume thereof, yields sufficient information to identify the molecular constituents and relative concentrations of even very complex mixtures. For example, nitrogen molecules in air will emit specific photon energies from lower and then higher energy emissions as the electrons move away from the electrode. The first low energy emissions will be relatively closer to the electrode and then higher energy molecular transitions will emit slightly further away. At the more distant regions of the plasma the nitrogen will emit from fully ionized and even doubly ionized transitions. At the extrema of the plasma from the electrode and later in the discharge pulse atomic nitrogen lines will be apparent due to molecular disintegration and atomic orbital transitions. Most of these excited states are highly unstable and will emit very quickly; however some fluorescence will occur with more stable stimulated states. With sufficient calibration and integration times, quantitative results can be obtained from spectral characteristics of the plasma volume. Emissions from various locations of the plasma volume are sampled at various times during and after a Trichel pulse.

As an example, near to the more negative electrode and early in the pulse we will see simple molecular stimulation of orbitals which will emit molecular spectra characteristic of molecules in the analyte. Further from the electrode, at that time point in the pulse there will be no emissions. As time progresses, about a nanosecond, the molecules will become ionized and ion emission will dominate the spectra at the same point in the plasma field. Later yet in the pulse, atomic emission will proceed. At a point further from the electrode, molecular emission will only occur very early in the pulse as free electrons gain greater kinetic energy levels and stimulate full or multiple ionization, deep orbital transitions, molecular dissociation, and thermal effects like rotation, vibration, and stretching modes imparted to the molecule and dominating emissions later in the pulse. Late in the pulse the last pulse electrons are accelerated with less energy due to field obscuration from charges in the gap which again stimulate lower energy transitions as one of the sequentially occurring train of energy gradients becomes negative. This is true further from the electrode also and transitions into fluorescent and chemical reaction emissions when the current falls at the end of the pulse. Each time at each spatial location within the pulse plasma will exhibit characteristics of particular molecular or atomic stimulation and emissions characteristics which are used to qualify, quantify, and separate emissions from a variety of materials within the gap.

The relatively low photonic emissions between Trichel pulses due to delayed fluorescence can be used to identify slowly fluorescing molecules like proteins, carbohydrates, hydrocarbons, and other fluorophores and radiators of interest. Molecular identification can be extended into larger biological molecules using mass spectroscopy operating on the plasma materials after plasma pulse molecular manipulation.

Many vibrational, rotational, and electronic states are excited during a plasma pulse; all such states are achievable including complete molecular disintegration and ionization states at some point in space and time of the plasma pulse. Charged sequentially occurring trains of energy gradients over time and space depend on the acceleration voltage waveform used leading up to, during, and after each pulse. In addition, these states can be modified through field interactions and collisional, photonic, and reactive effects with other materials, the electrodes or the containment chamber walls if a containment reaction chamber 16 is used. The transitions leading to photonic emission are thought to be defined by the discrete quantum states before photon emission as well as the resulting quantum states after photon emission. This difference equals the photon energy with some alteration for thermal stabilization energy effects like quenching and Doppler shifting. In addition, rotation of molecular ions will emit radio frequency energy dependent on the geometry of the molecule, ionized state, the moment of inertia, and also the spatial net charge distribution of the ion.

By inserting the plasma fields into optical resonators 56, a laser pumping is achieved and laser coherent emission is inherently available for arrays of these discharge plasmas 28 as in FIG. 9. Such laser action directs the emission energy coherently through space to remote detectors enabling remote determination of chemical and structural information as well as highly refined multi-frequency, also called multi-color, laser beams for information passage, excitation, aesthetic effects, optical pumping, ablation applications, and fluorometry. In fluorometry applications, excitation photons stimulate electrons to higher energy states in a variety of vibrational states. Molecular and other interactions are thought to relax these excited states to the lowest vibrational states of the stimulated orbital condition. The electrons then transition to one of the vibrational levels in respective ground states while emitting a photon having an energy level characteristic of the emitting bond or orbital change. These vibrational state energy differences enable a variety of photon emission energies just below the energy of that due to electronic transition to the lowest vibration state of the ground state of the molecule. This variability of the emission spectrum can give information about the shape of the quantum well as well as mask the detail of the electronic transition energy wavelengths and is akin to Raman methods.

This invention can make absolute evaluation of the identity of the specific molecular species possible through predictions of the Franck-Condon principle, which make identifications via correlations of spectral peak amplitudes available. Looking for specific predicted emissions allows discovery of materials not previously characterized in a plasma instrument. Pinene, an aromatic, naturally occurring oil has specific transitions predicted by the Franck-Condon principle, and were discovered in the plasma emissions at specific times of the pulse and at specific locations within the pulse. A large variety of common analyte materials follow this predictive capacity and may be used to identify unknown emission characteristics and assign chemical identities in this method.

Raman scattering data may also be used to analyze spectral emissions of the instant invention. Here, a monochromatic light source typically used in Raman studies may be the separated monochromatic plasma emissions from the Trichel pulses. In this embodiment, the emissions due to Trichel pulses in the presence of an analyte are analyzed for spectral content as a function of the time separation of the pulse from initiation as well as the spatial distribution of ultraviolet, visible, and infrared emissions within the plasma. These spectral distributions may also be done with time-varying functional gap potentials instigating variable instantaneous gap currents and gap ion and charge clearance times. A spectral scan at each time step and position within each pulse, which encompasses many repeating plasma discharges, yields time and space spectra within each time step and position chosen. The time and space spectral intensity series can be Fourier transformed into spatial and temporal domain frequencies that are correlated with known series by calibration, or predictive correlations by energetics predicted by the Franck-Condon principle.

Below a breakdown or cascade potential difference at which a Trichel pulse occurs, there is very little current flow across a gap. At the breakdown potential there will occur occasional typical Trichel pulses exhibiting small average currents and pulsing optical emissions. As the potential increases further, the Trichel pulses remain similar in magnitude and duration, but occur more often, triggered by random or intentional timed exogenous ionizing or surface electron ejection events. The threshold potentials applied to the gap electrodes for developing Trichel pulses is generally dependent on the material of the electrodes, electrode geometries, exogenous stimulating events, and the attendant electron binding energies of the materials in the gap. The homogeneity of the electrode surfaces is important in defining the threshold potential; however in practice with this invention it is not crucial to the operation above threshold potentials beyond the need for stability to avoid contamination of the gap environment with sputtered materials from the electrodes, The geometries of the electrodes has a major impact on the extent and activities of the Trichel discharge plasma. Parallel plate electrodes as in FIG. 2 will require very high potentials to initiate plasma pulses. However, variations in a high curvature negative point electrode 30 to planar or extended, lower curvature surface electrode 24 configuration as in FIG. 3 will increase the electric field gradient near a point electrode 30 by several orders of magnitude. For example, a 10 kilovolt negative point to ground or zero voltage potential planar electrode 24 can easily reach electric field strengths of millions of volts per meter near the point of electrode 30. This causes the plasma to form in very small regions near the point, approaching millions of cubic micrometers or smaller. The sharper the point, the higher the relative field strength gradients near the point tip 30 nearest a planar low curvature positive counter electrode 24 due to electric field convergence as in FIG. 3.

Once a series of Trichel pulses are formed by applying a sufficient potential difference between the point electrode 30 and planar electrode 24, elements of the emission spectrum are recorded during the course of each about <1 nanosecond time steps from the beginning to end of each plasma pulse with great accuracy, establishing a time bin for each time step. This process integrates spectral energy distributions of many pulses into equivalent time bins. The data set can then be considered as the spatial and temporal development of the spectra which is different for every material. Once specific spectral lines are identified as due to analyte, the evolution of that line in time at each point in space is definitive for identification. Integration of the spectral magnitudes correlates with the quantity of the analyte. The wide variety of highly specific spectral lines stimulated during the pulses allows the identification and quantification of many different materials within the gap. This results in an integrated four dimensional data set of linear photon spectral intensities against time step from Trichel pulse onset against physical location within the gap. The integration is particularly useful for analysis at very low concentrations and when high accuracy is necessitated. The earliest time step data evidences differently ionized and stimulated orbitals than later time steps due to more energy states exhibiting more high average energy collisional interactions, vibrational stabilization, and differing transient magnetic fields as well as varying impressed fields. Each analyte species evokes a different emission pattern which can be described and correlated with location in the gap and time from pulse initiation. The combined effects of these transform correlations is increased resolutions, spectral separations, noise elimination, and precision of measurement allowing deconvolution of many component spectra from the integrated spectral signatures for specific chemical identification and quantification. While this is a complex computational or optical effort, signal acquisition and processors are fully capable of handling the data stream in near real time for library correlations or predictive analysis.

Individual species will provide maximum characteristic spectral line signatures at specific times and locations within the plasmas when and where the signal to noise ratio will be maximized for each chemical dependent spectral line, depending on the ionization energies, band gaps, and molecular characteristics as well as those of other materials in the gap. These best case correlations will be apparent from the deconvolution of the complete data set of the complete power spectra. Post processing of indicated maximal signature data frames can allow more accurate quantification of interesting molecules, fragments, or chemical reaction intermediates, precursors, and products within the plasma discharge. This allows for analysis of intermediate states within the plasma for elucidation or encouragement of specific chemical activities.

Simpler, cheaper, and faster applications for visualization of the spectra is by electro-optical multiplication of the spectral photons by impacting analytic spatially dispersed spectral photons onto a phosphor screen which integrates incoming photons into omnidirectional photoelectric electrons inside an accelerating field vacuum tube. Accelerating this electron can increase its energy sufficiently to be seen on an output phosphor screen with the naked eye, lit up with phosphorescence from the impinging electrons, especially when electrons are multiplied with an MCP (multichannel plate), very much like a multichannel PMT (photomultiplier tube).

This is known as photonic intensification and the device is termed an intensifier and is designated as GenII intensifiers when the MCP is used and may be ITAR (International Traffic in Arms Regulations) controlled by law if exported. This proprietary spectral output phosphor screen and intensifier system can be optically and electronically integrated to produce easily recognizable patterns for particularly dangerous, noxious, toxic, explosive, leaking, contaminating, spreading, radioactive, and other substances of interest to the human user, who simply views the data. The data acquisition, processing, correlating, and rational output mechanism can easily be done by a computer or smart phone as well.

The intensifier technology is also the key to allowing this method to time sample the few nanosecond Trichel pulses, as modern intensifers can shutter or gate the optical signals in less than 1 nanosecond open or closed. Thus a simple or complex time step ramp from the trigger to the intensifier gating open and then programmed to close at prescribed delay times allows both single valued delays as well as programmed functional variable delays.

Further value of the intensifier application here is that geometric masking or filtering of the intensifier MCP, phosphor input screen, spectral translation pathways, or output screens can obviate damage to electronic or optical components due to extreme dynamic ranges of the spectral signals as well as simplifying the spectral content to make the unknown analyte emissions the most apparent to the user.

Alternatives to intensifier use for visualization 14 are PMT (Photomultipier tube), super-cooled EMCCD (electron multiplied ccd), and long integration times on solid state detectors at ambient temperatures. These all introduce undesirable limitations on the invention performance. PMTs are very accurate and fast, but impart a multi-millisecond delay between photons and output response which obviates the time step data collections without very careful predictive triggering phasing. They also cannot be triggered for very short acquisition windows and they are not cheap or readily available as large arrays as desired for fast and low cost operations of this subject invention. An embodiment used a scanning monochromator as the optical receiver, and which is ported out to a single PMT for readout as the visualizer 14. Very fast oscillographic renderings of individual spectral line pulse shapes were the first data of the phenomena discovered in this method invention.

In the atmosphere, nitrogen emissions predominate and driving or integrating plasma emissions to sensible levels for minor constituents will overdrive the nitrogen emissions, causing damage or signal overload to components, especially phosphor screens. Atomic nitrogen lines are shown in FIG. 10. This is also true for a variety of strong emitters such as oxygen or other molecular species that may be in the plasma emission volume. One approach may be to simply letting the damage accumulate and not use those spectral regions for analysis. Alternatively, masking, altering coatings, or filtering can be spatially applied to the intensifier input window, MCP, light pathways, or output window at spectral locations with damaging signal levels. The spectral signals can also be filtered or blocked within the spectral dispersion optical path of the invention as emissions are separated by wavelength or even blocked with band pass filters before the spectrometer. Yet another approach may be to mix the analyte with a pure gas having low spectral emissions. Another advantage here is that the known, pure gas emissions can easily be filtered out.

Different energy gradient conditions stimulate vibrational/rotational energy levels and will evidence with multiple photon emission energy peaks which should trend with collisional deactivation. Predominant Franck-Condon principle fulfillment tends to be from primarily the lowest vibrational excited electronic state as each plasma pulse ages from inception to extinction over duration of a plasma pulse. These amplitude values can be used to elucidate excitation state lifetimes, molecular concentrations and coupling, stereoisomerism details, atomic species, and details about molecular structures. Signature libraries are developed by passing known concentrations of known chemical species through the gap under controlled circumstances and creating a multidimensional plasma emission spectral response library for emission spectra correlating with gap spatial and plasma pulse time course axes. These signatures can then be correlated with scan results for positive quantifiable correlations for a large variety of known chemicals and their mixtures. After correlation filtering of known and discovered constituents, any remaining uncorrelated energy will be ascribed to unknown constituents.

In summary, we insert or induct a target analyte with or without a carrier material, into an electrode gap with sufficient potential difference across the gap to initiate Trichel pulses. These pulses give rise to spatial, spectral, and temporal variations in photon emission energies which are signatures ascribable to particular constituents included within the target analyte.

Having thus described my invention and the manner of its use, it should be apparent to those skilled in the relevant arts that incidental changes may be made thereto that fairly fall within the scope of the following appended claims, wherein I claim:

1. A method for detecting all components of an unknown analyte and concentrations of said components in said unknown analyte comprising:
   establishing a sequentially occurring train of Trichel pulses in the presence of said unknown analyte,
   obtaining from said train of Trichel pulses, photon emissions from each component of said unknown analyte and an intensity of said photon emissions,
   from said photon emissions, determining what each component is and from said intensity of photon emission from each said component determining concentration of said each component of said unknown analyte.

2. The method of claim 1 wherein said establishing said sequentially occurring train of Trichel pulses further comprises establishing said sequentially occurring train of Trichel pulses in an electrical energy gradient so that one side of each Trichel pulse of said sequentially occurring train of Trichel pulses has a lowest electrical energy level and an opposite side of each said Trichel pulse has a highest electrical energy level, thereby separating in distance and by wavelengths photon emissions of each said component from photon emissions of other said components within each said Trichel Pulse in accordance with said electrical energy gradient.

3. The method as set forth in claim 2 wherein said obtaining photon emissions further comprises, for each said component of said components, obtaining said photon emissions from a respective discrete, unique location in said Trichel pulses corresponding to a respective unique electrical energy level of said electrical gradient where said each component of said unknown analyte is emitting photons.

4. The method of claim 3 wherein said obtaining photon emissions from said discrete, unique location further comprises observing said discrete, unique location in a plurality of said Trichel pulses, and integrating intensity of photons from said discrete, unique location in order to increase a signal to noise ratio of said photon emissions from said discrete, unique location.

5. The method of claim 3 wherein said obtaining photon emissions further comprises sequentially scanning different discrete, unique locations in said Trichel pulses for obtaining said photon emissions at successively higher or lower energy levels.

6. The method of claim 5 wherein said scanning further comprises scanning said unique locations in about 10 micron increments.

7. The method of claim 3 wherein said obtaining spectral lines from a plurality of different locations in said Trichel pulses further comprises obtaining said spectral lines during discrete time periods of less than a complete Trichel pulse duration.

8. The method of claim 3 wherein said obtaining photon emissions from a respective, discrete location further comprises obtaining said photon emission from about a 1 micron region of said Trichel pulses.

9. The method as set forth in claim 2 further comprising using a Trichel pulse trigger externally applied directly to electrodes generating said electrical energy gradient or externally applied to a gap between said electrodes for initiating said sequentially occurring train of Trichel pulses.

10. The method of claim 1 wherein said photon emissions of said unknown analyte are obtained as a plasma emission spectrum image, and storing said plasma emission spectrum image in a computer memory.

11. The method of claim 10 further comprising using a computer to correlate a stored said plasma emission spectrum image with a plurality of stored plasma emission spectrum images of known analytes and concentrations of said known analytes and present correlations as determinations of said unknown analyte and concentrations of components of said unknown analyte.

12. The method as set forth in claim 1 wherein said obtaining photon emissions further comprises obtaining said photon emissions during a predetermined time interval of discrete ones of said Trichel pulses wherein said predetermined time interval is selected to detect photon emissions of a duration longer than a respective Trichel pulse, for detecting fluorescence of at least one molecular species of said unknown analyte.

13. The method as set forth in claim 1 wherein said obtaining photon emissions further comprises obtaining said photon emissions during a predetermined time interval of discrete ones of said Trichel pulses wherein said predetermined time interval is selected to detect photon emissions of a duration shorter than a respective Trichel pulse, for detecting photon emissions of at least one atomic species of said unknown analyte.

\* \* \* \* \*